(12) United States Patent
Gupta et al.

(10) Patent No.: US 8,513,206 B2
(45) Date of Patent: Aug. 20, 2013

(54) CROSSLINKED PEI NANOPARTICLE TRANSFECTION AGENTS FOR DELIVERY OF BIOMOLECULES WITH INCREASED EFFICIENCY

(75) Inventors: Kailash Chand Gupta, Delhi (IN); Pradeep Kumar, Delhi (IN); Archana Shami, Delhi (IN); Atul Pathak, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 817 days.

(21) Appl. No.: 12/181,798

(22) Filed: Jul. 29, 2008

(65) Prior Publication Data

US 2010/0029750 A1    Feb. 4, 2010

(51) Int. Cl.
*A61K 48/00*    (2006.01)
*A61K 9/50*    (2006.01)

(52) U.S. Cl.
USPC .......................... 514/44 R; 424/497; 424/498

(58) Field of Classification Search
None
See application file for complete search history.

(56) References Cited

U.S. PATENT DOCUMENTS

| | | | | |
|---|---|---|---|---|
| 5,153,024 A | * | 10/1992 | Schutyser | 430/315 |
| 5,817,883 A | * | 10/1998 | Briggs et al. | 568/454 |
| 6,689,820 B2 | * | 2/2004 | Muranaka et al. | 521/30 |
| 6,858,203 B2 | * | 2/2005 | Holmes-Farley et al. | 424/78.11 |

OTHER PUBLICATIONS

Swami, et al. (2007) Biochemical and Biophysical Research Communications, 362: 835-41.*
Swami, et al. (2009) International Journal of Pharmaceutics, 374: 125-38.*

* cited by examiner

*Primary Examiner* — Robert M Kelly
(74) *Attorney, Agent, or Firm* — Ladas & Parry LLP

(57) ABSTRACT

The present invention relates to a novel crosslinked polyethylenimine (PEI) nanoparticle based nucleic acid transfection agent wherein the crosslinker is having carbon chain in the range of C2 to C8, ranging between 3.27-19.8%, having the size of nanoparticle ranging between 20-600 nm and zeta potential ranging from +5 to 50 mV.

12 Claims, 12 Drawing Sheets

Figure 1A:
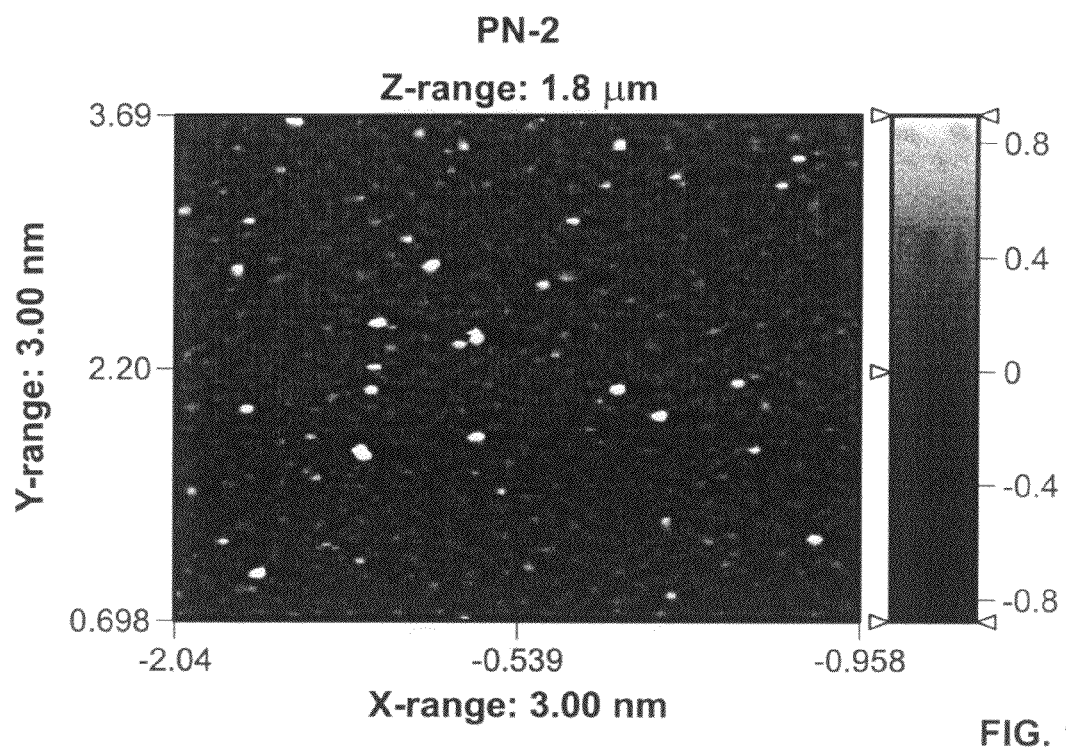
Figure 1B:
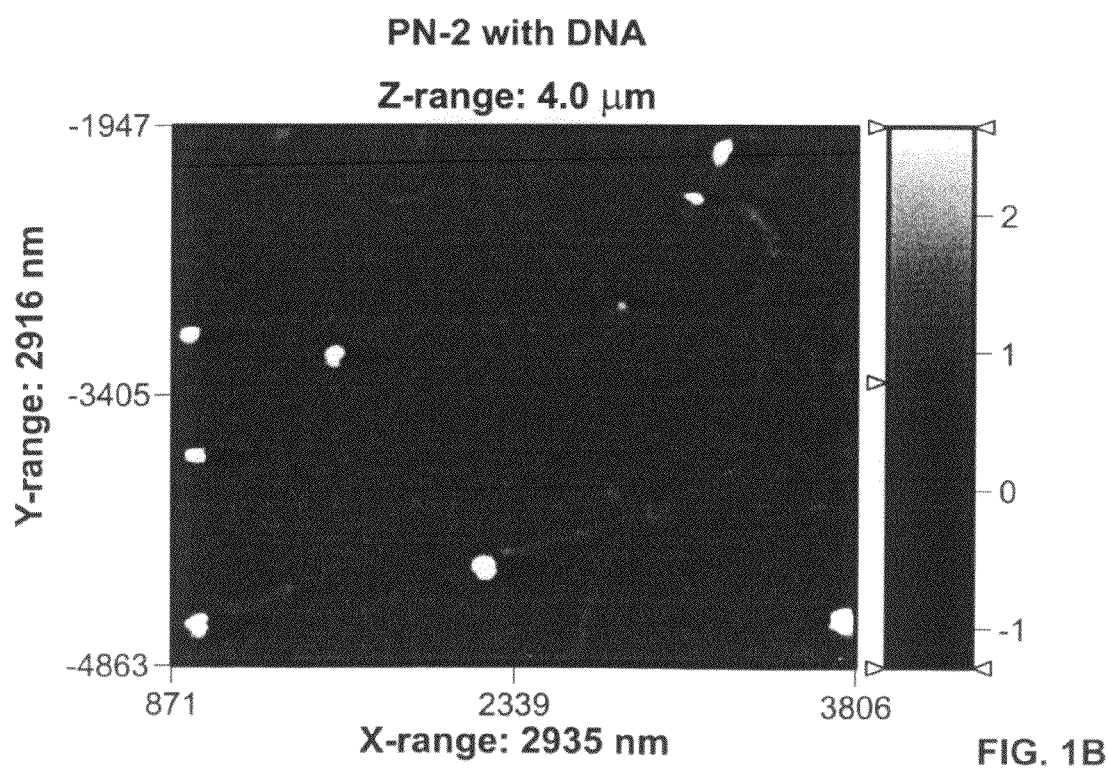
Figure 1C:
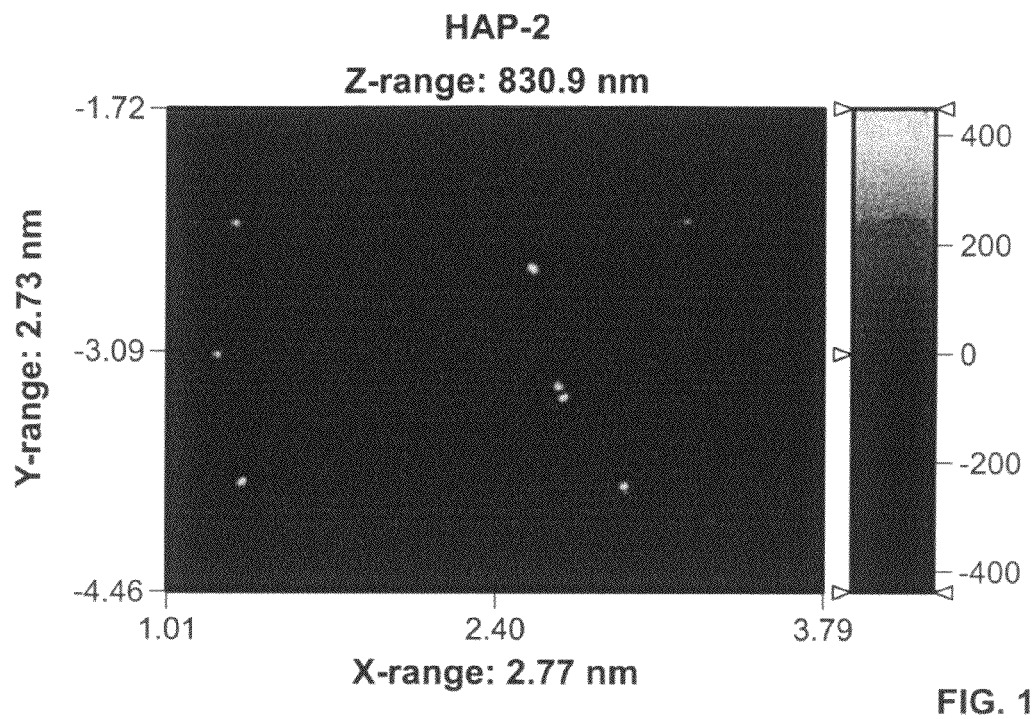
Figure 1D:
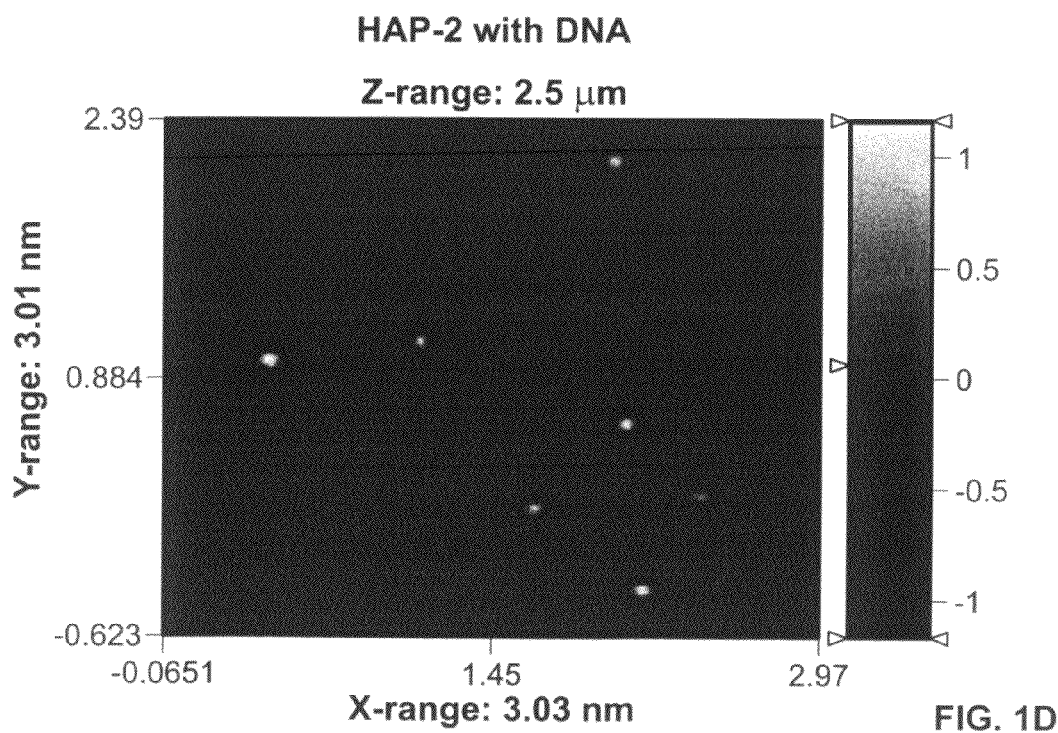

CROSSLINKED PEI NANOPARTICLE TRANSFECTION AGENTS FOR DELIVERY OF BIOMOLECULES WITH INCREASED EFFICIENCY

The invention relates to the development of non-viral cationic vectors for the delivery of genetic material, more accurately for delivery of bioactive molecules such as nucleic acids (DNA, siRNA, miRNA, etc.) to the cells (in vitro and in vivo).

BACKGROUND OF THE INVENTION

A variety of materials (i.e., cationic lipids, polymers: natural and synthetic and peptides) have been utilized to fabricate non-viral delivery systems (M. J. Tiera et al, Curr. Gene Ther. 6 (2006) 59-71,13) which have several advantages in terms of safety, ease of preparation, reproducibility, ability to carry large nucleic acid constructs and stability (X. Gao et al, AAPS J. 9 (2007) E92-E104). Cationic lipids and cationic polymers for gene delivery may cause toxic effect in vitro and in vivo. For example lipoplexes caused several changes to cells, which included cell shrinking, reduced number of mitoses and vacuolization of the cytoplasm (K. Lappalainen et al, Pharm. Res. 11 (1994) 1127-1131). Cationic polymers, viz., polyethylenimine (PEI), polyamidoamine (PAMAM), polypropylenimine (PPI), poly-L-lysine (PLL), cationic dextran, polyallylamine (PAA), dextran-oligoamine based conjugates and chitosan, (M. D. Brown et al, Int. J. Pharm. 229 (2001) 1-21; H. Hosseinkhani et al, Gene Ther. 11 (2004) 194-203.), are amongst the preferable materials for the preparation of non-viral vectors in terms of their long-term safety and biocompatibility. PLL, PAA and many others were abandoned due to its low transfection efficiency and higher cytotoxicity. Dextran-oligoamine based transfection in a wide range of cell lines is very low in comparison to other cationic vectors based on PEI, dendrimers etc. Of these, PEI is one of the most successful and widely studied gene delivery polymers due to its membrane destabilization potential, high charge density (DNA condensation capability) and ability to protect endocytosed DNA from enzymatic degradation, thus perform DNA transfer efficiently into the cells (U. Lungwitz et al, Eur. J. Pharm. Biopharm. 60 (2005) 247-266). Branched PEI contains primary, secondary and tertiary amines in a ratio of 1:2:1 with pKa values spanning around the physiological pH, providing remarkable buffering capacity. The primary amines are mainly responsible for high degree of DNA binding, but contribute maximum toxicity during transfection, while the secondary and tertiary amino groups provide good buffering capacity to the system (X. Gao et al, Mol. Ther. 11 (2005) S427-S428). Though high charge density of the system increases the transfection efficiency, it simultaneously contributes to increased cytotoxicity. Actually, the efficacy of the transfection system is a sweet compromise between the transfection efficiency and the cytotoxicity. Several research groups have attempted to reduce the charge associated toxicity of PEI either by incorporating various ligands like peptides, polyethylene glycols, polysaccharides or by substituting the amines with imidazolyl and acyl functions (U. Lungwitz et al, Eur. J. Pharm. Biopharm. 60 (2005) 247-266; S. Patnaik et al, J. Control. Release 114 (2006) 398-409; A. Swami et al, Int. J. Pharm. 335 (2007) 180-192; S, Nimesh et al, Int. J. Pharm. 337 (2007) 265-274). However, these modifications result in partial blockage of the net amino charge on PEI, thus making a compromise on transfection efficiency. These ligands react with amines of PEI by shielding the charge which is responsible for the cytotoxicity of PEI as well as the DNA binding ability and in turn the transfection efficiency of PEI, thus making a compromise in a way.

There is a need to design a system based on cationic polymers where, primary amino content could be kept to minimum and secondary, tertiary and quaternary content could be increased to obviate the drawbacks listed above and reduce cytotoxicity.

In the present invention, in order to address the problem of cytotoxicity in PEI and to improve upon the transfection efficiency, PEI nanoparticles have been prepared using crosslinkers such as, 1,4-butanediol digycidyl ether (bisepoxide) and 1,6-hexandial (bisaldehyde) which reduces the charge dependent toxicity of native PEI (25 kDa).

The novelty of the invention is in the crosslinkings which do not alter the net charge of the PEI system, rather it partially converts the primary amines (main source of toxicity) to secondary, the secondary to tertiary amines (which play important role in buffering capacity) and/or tertiary to quaternary amines making the highly toxic PEI into transfectionally competent system.

Another novelty of the present invention is in providing nanoparticle based efficient polymeric transfection agent by converting the amine moiety of the cationic polymer from primary to secondary to tertiary and/or further to quaternary state.

OBJECTS OF THE INVENTION

The main object of the present invention is to develop a nanoparticle based efficient polymeric transfecting agent with reduced cytoxicity.

Another objective of the present invention is to provide a nanoparticle based efficient polymeric transfection agent with reduced toxicity and essentially consisting of conversion of the amine moiety of the cationic polymer from primary to secondary to tertiary and/or further quaternary state Still another objective of the present invention is to provide a simple, efficient and economical process of preparation of the transfection reagents.

Another objective is to provide carrier systems which will efficiently deliver genes in cells.

A further objective is to provide transfection reagents which will transfect a variety of cell lines efficiently with minimal cytotoxicity.

SUMMARY OF THE INVENTION

The primary amino groups present in the PEI system contribute towards cytoxicity whereas secondary and tertiary amino groups help in enhancement of buffering capacity and ultimately improve the transfection efficiency. Therefore, there is a need to design a nanoparticle based transfecting agent based on cationic polymers where, primary amino content could be kept to minimum and secondary, tertiary and quaternary content could be increased and would be useful for efficiently delivering genetic materials with low cytotoxicity and cell damage.

Accordingly, the present invention provides a novel crosslinked PEI nanoparticle based transfection agents for delivery of biomolecules. More specifically the said transfection agents, PEI crosslinked with the crosslinker 1,4-butanediol diglycidyl ether or 1,6-hexanedial can deliver various nucleic acids such as plasmid DNA, siRNA, genomic DNA, synthetic oligonucleotides and similar into the cells and having reduced cytotoxicity with several fold transfecting efficiency as compared to native PEI and commercially available transfection agents.

In an embodiment to the present invention, the crosslinked cationic polymer, polyethylenimine PEI and the crosslinker having carbon in the range of C2 to C8, preferably 1,4-butanediol diglycidyl ether or 1,6-hexanedial with the crosslinker content ranging between 3.27-19.8% having the size of nanoparticle is ranging between 20-600 nm and zeta potential ranging from +5 to 50 mV.

In another embodiment to the present invention, the crosslinker used is 1,4-butanediol diglycidyl ether, to convert toxic primary state of amine of the cationic polymer to less toxic secondary, tertiary and quaternary state respectively resulting into minimal cytotoxic transfecting agent.

In still another embodiment to the present invention, the crosslinker used is 1,6-hexanedial to convert the toxic primary state of amine of the cationic polymer to less toxic secondary amines resulting into minimal cytotoxic transfecting agent.

In yet another embodiment to the present invention, the transfection efficiency of polymeric transfection agent (PEI crosslinked with 1,4-butanediol diglycidyl ether) is 4.7 fold with respect to native PEI in case of HEK293 cells, 2.2 fold w.r.t. PEI in case of COS-1 cells and 3.8 fold w.r.t. PEI in case of HeLa cells.

In an embodiment to the present invention, wherein the transfection efficiency of polymeric transfection agent (PEI crosslinked with 1,6-hexanedial) is 6.1 fold with respect to PEI in case of HEK293 cells, 3.5 fold w.r.t. PEI in case of HeLa cells; 1.9 fold w.r.t. PEI in case of A549 cells.

In an embodiment to the present invention, the transfection efficiency of polymeric transfection agent is several fold as compared to commercially available transfection agents.

In still another embodiment to the present invention, the transfection efficiency of polymeric transfection agent (PEI crosslinked with 1,4-butanediol diglycidyl ether) as compared to commercial transfection agents is 2.9 fold w.r.t. Fugene™ and 2.1 fold w.r.t. Lipofectainine2000™ in case of HEK293 cells.

In an embodiment to the present invention, the transfection efficiency of polymeric transfection agent (PEI crosslinked with 1,6-hexanedial) as compared to commercial transfection agents is 2.1 fold w.r.t. gene porter 2™, 2.2 fold w.r.t. Fugene™ and 3.6 fold w.r.t. Superfect™ in case of HEK293 cells.

In an embodiment to the present invention, wherein the cell viability of polymeric transfection agent (PEI crosslinked with 1,4-butanediol diglycidyl ether) is 92% (57% for PEI) in case of HeLa cells; 80% (63% for PEI) in case of HEK293 cells; 93% (65% for PEI) in case of COS-1 cells and 70% (50% for PEI) in case of A549 cells.

In an embodiment to the present invention, the cell viability of polymeric transfection agent (PEI crosslinked with 1,6-hexanedial) is 99% (60% for PEI) in case of HEK293 cells; 98% (58% for PEI) in case of HeLa cells and 97% (53% for PEI) in case of A549 cells.

Another aspect of the invention is use of polymeric nanoparticle based transfecting agent for efficient delivery of various nucleic acids such as plasmid DNA, siRNA, genomic DNA, synthetic oligonucleotides and similar into the cells.

The invention also provides a process of preparation of nanoparticle based efficient polymeric transfection agent of the present invention having reduced toxicity and essentially consisting of conversion of the amine moiety of the cationic polymer from primary to secondary, secondary to tertiary and/or further to quaternary state and consisting of the steps of:

a) reacting cationic polymer polyethylenimine (PEI) (15-30 kDa) with homo-bifunctional cross linker having carbon in the range of C2 to C8, preferably 1,4-butanediol diglycidyl ether and 1,6-hexandial (2-20%), at a temperature ranging between 25-90° C., in a solvent selected from a group consisting of water, dioxan, tetrahydrofuran, dimethylformamide, dimethylsulphoxide, and acetonitrile, for a period ranging between ½ hr-10 hr, b) adding reducing agent in the above reaction mixture (step a) wherein the crosslinker used is 1,6-hexanedial c) Reducing the volume of the reaction mix to half under reduced pressure to form stable nanoparticles, d) subjecting the reaction mixture to dialysis against water for 2-5 days and concentrating the dialysed mixture to obtain the solid nanoparticles e) characterizing the prepared nanoparticles for surface charge, size and morphology, f) evaluating cytotoxicity of the prepared nanoparticles, g) assessing the transfection efficiency of the prepared nanoparticles in various cell lines.

In another embodiment of the invention the reducing agent used is selected from sodium borohydride, sodium cynoborohydride. Lithium borohydride, lithium cynoborohydride, etc

BRIEF DESCRIPTION OF THE DRAWINGS, FIGURES AND TABLES

The above-mentioned objects and advantages of the present invention will be more clearly understood when considered in conjunction with the accompanying table and figures, in which:

Table-1: Measurement of particle size and zeta potential of PEI and bisepoxide crosslinked PEI nanoparticles (PN), weight by weight ratio of nanoparticle to DNA w/w=5). PEI: polyethyleneimine; $dH_2O$: double distilled water at pH 7.00; Np: nanoparticles.

Table-2: Measurement of particle size and zeta potential of PEI and bisaldehyde crosslinked PEI nanoparticles (HAP), weight by weight ratio of nanoparticle to DNA w/w=1). PEI: polyethyleneimine; $dH_2O$: double distilled water at pH 7.00; Np: nanoparticles.

Table-3: Percent cross-linking of primary amines in bisepoxide crosslinked PEI (25 kDa) nanoparticles (PN) by NMR.

Table-4: Percent cross-linking and estimation of primary amines in bisaldehyde crosslinked PEI (25 kDa) nanoparticle (HAP) by TNBS assay.

Table-5: $IC_{50}$ value for bisaldehyde crosslinked PEI (25 kDa) nanoparticle (HAP)

FIG. 1 AFM images of PEI nanoparticles,
(A) native PN-2 (32-40 nm)
(B) DNA loaded PN-2 nanoplexes (55-60 nm)
(C) native HAP-2 ((40-55 nm)
(D) DNA loaded HAP-2 nanoplexes ((60-75 nm)

Figure 2A:
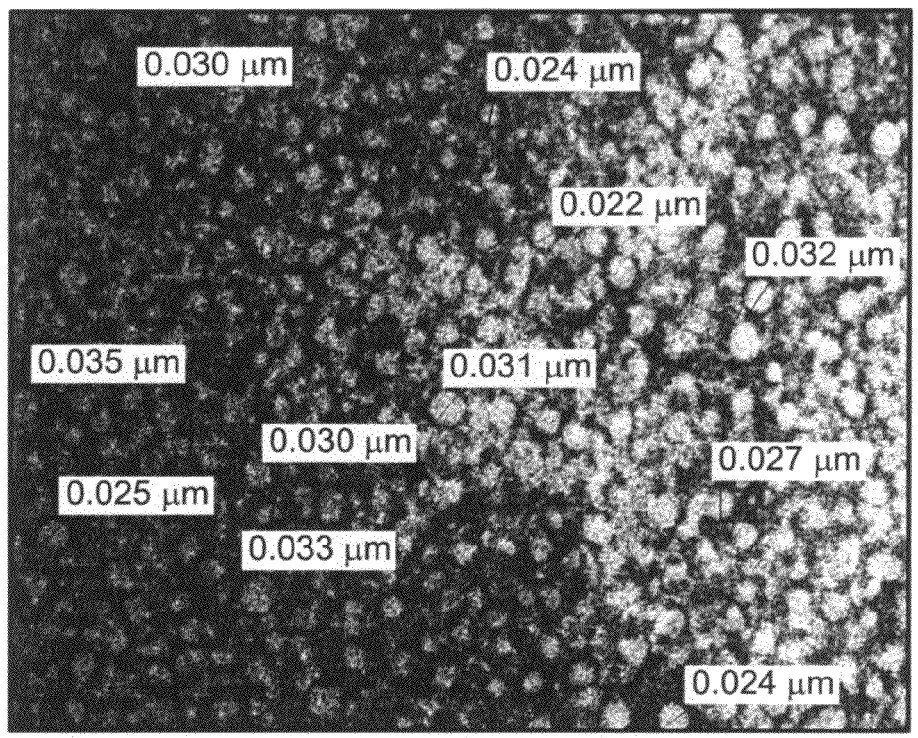
Figure 2B:
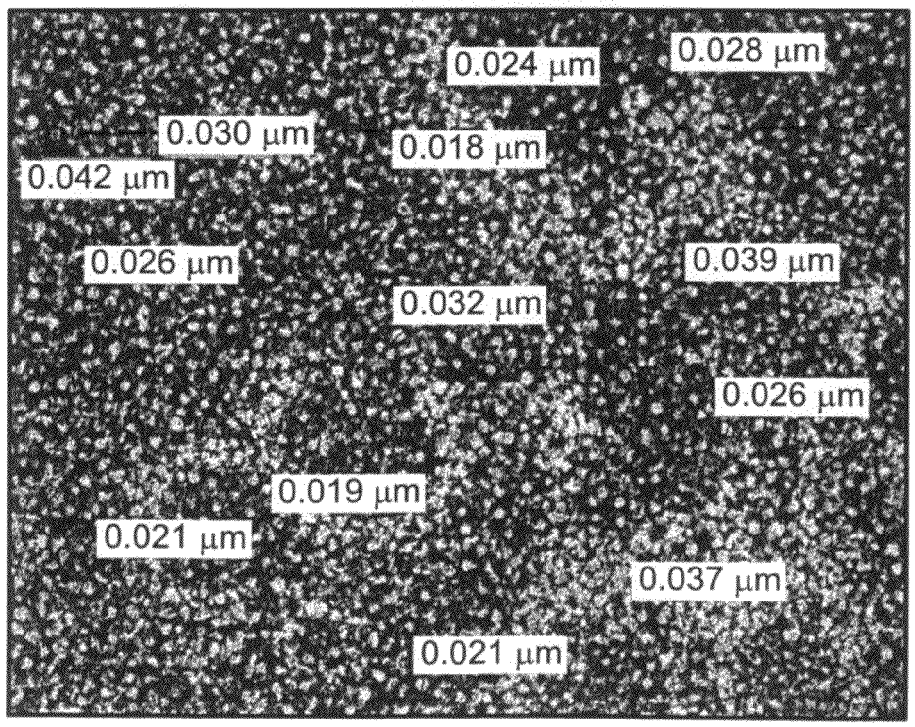

FIG. 2 Size distribution obtained by TEM images of PEI nanoparticles,
(A) PN-2 nanoparticles with average size of ~35 nm
(B) PN-3 nanoparticles with the average size of ~27 nm.

Figure 3:
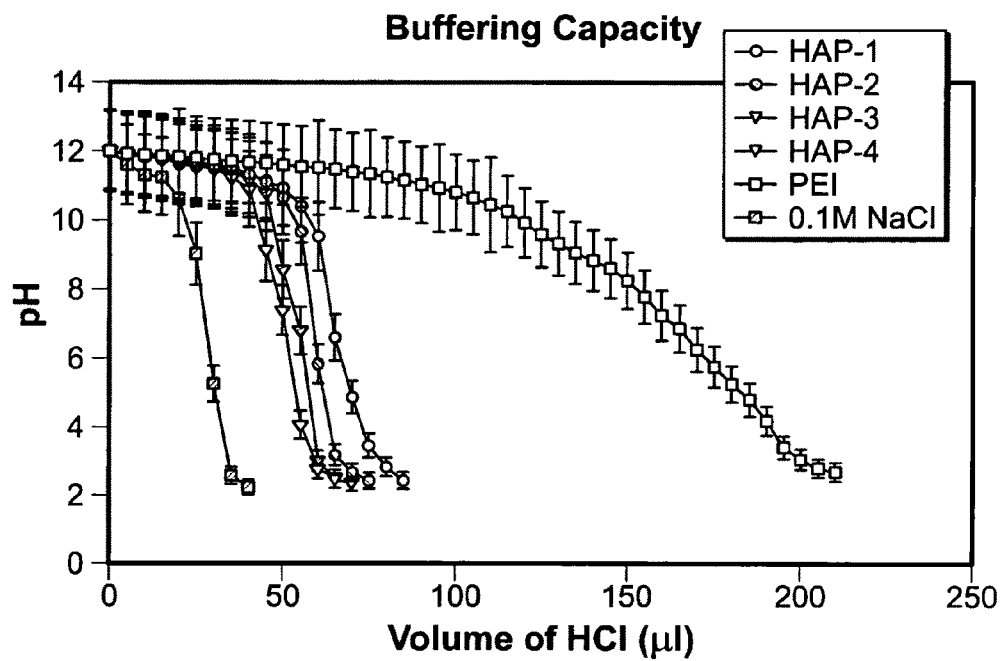

FIG. 3 Buffering capacity of PEI and PEI nanoparticles (HAP). Error bars represents +/− standard deviation from the mean.

Figure 4:
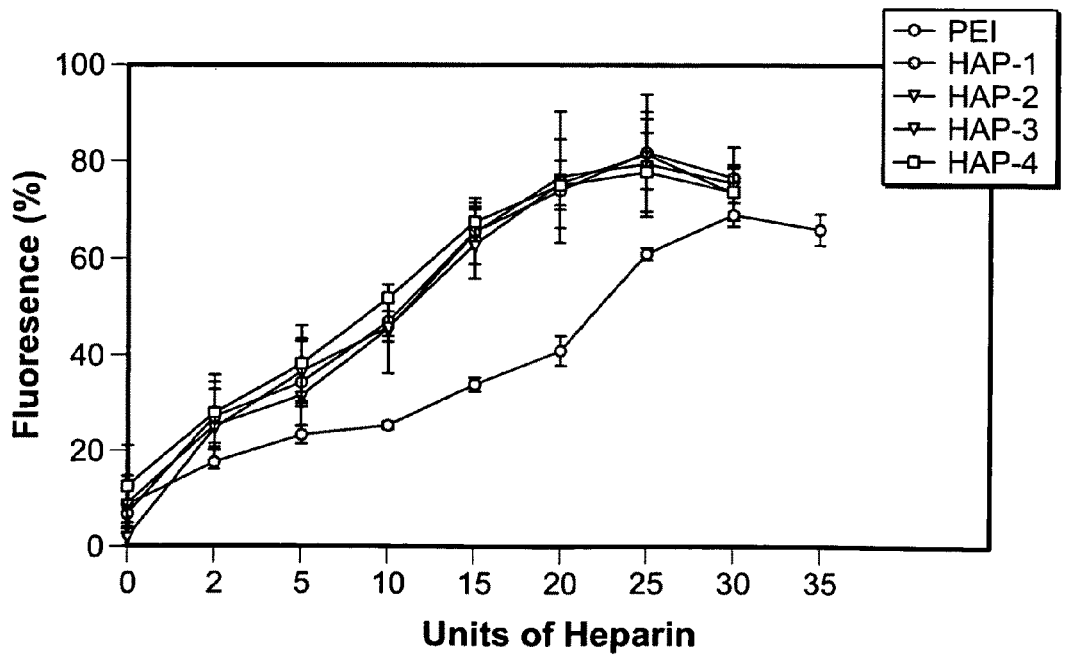

FIG. 4 DNA release assay of PEI and HAP nanoparticles. DNA (15 µg/mL) was mixed with EtBr (1 µg/mL) and fluorescence measured using nanodrop 3300, at blue led (506 nm excitation and 610 nm emission) set to 100%. Background fluorescence was set 0% using EtBr (1 µg/mL) solution alone. To allow complete displacement of the DNA, from PEI nanoparticle/DNA complexes (w/w ratio of 1), anionic polysaccharide, heparin added stepwise in aliquots to each sample and incubated for 20 min after each addition before reading the fluorescence. Condensation curves were constructed and results were expressed in terms of percent of the maximum fluorescence signal obtained by ethidium bromide/DNA complex, in the absence of any competition.

Figure 5:
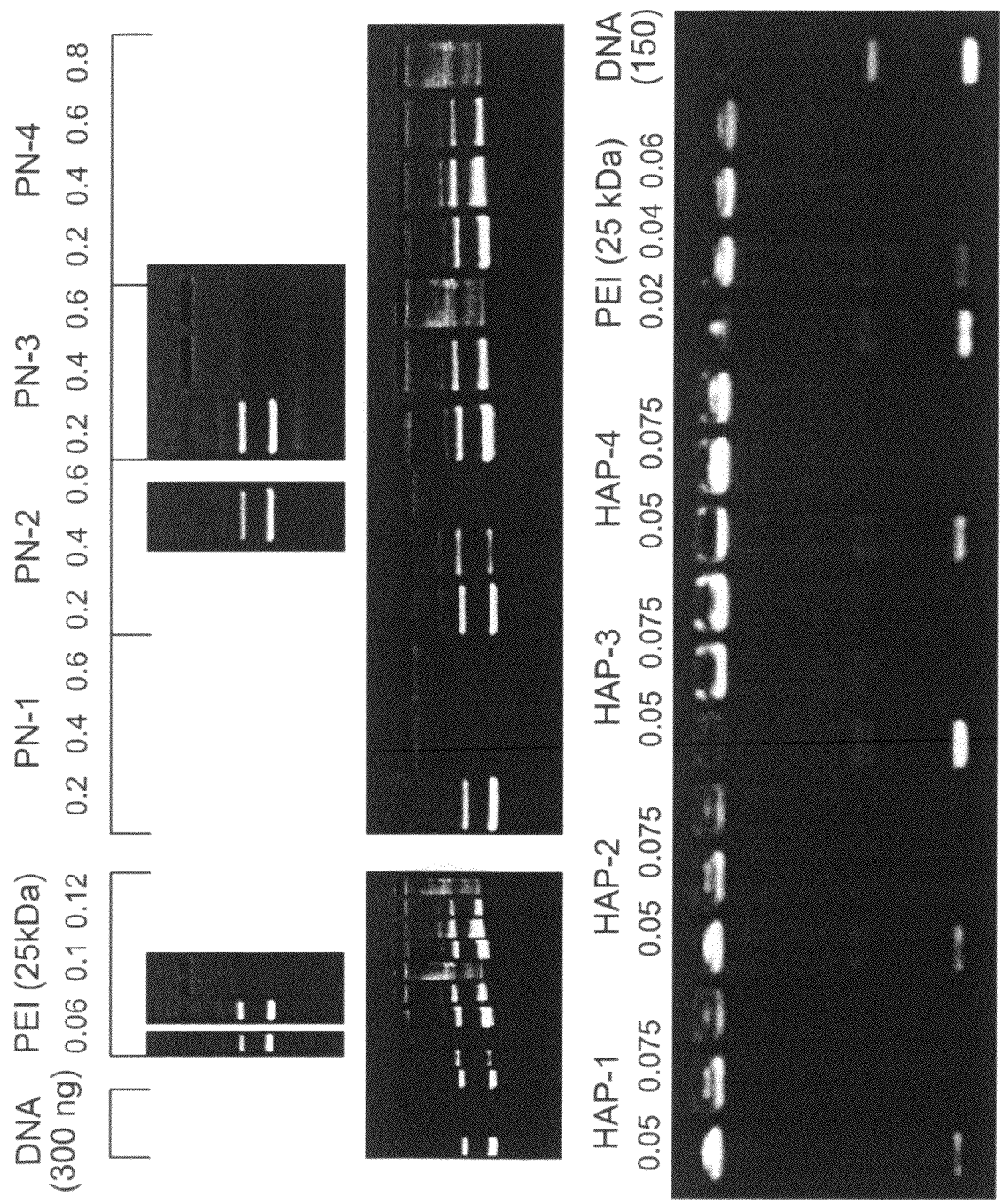
Figure 6A:
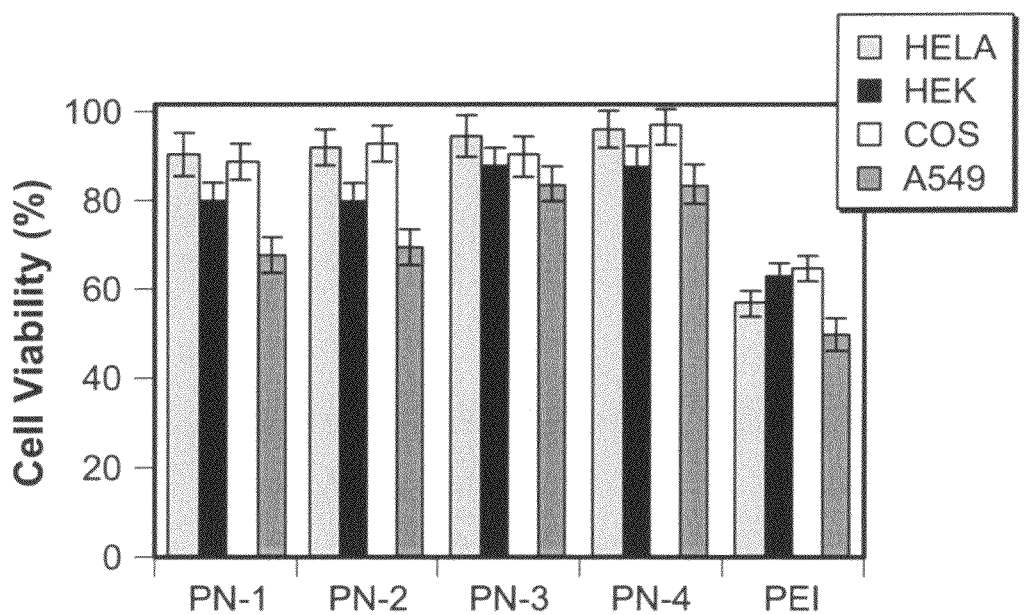
Figure 6B:
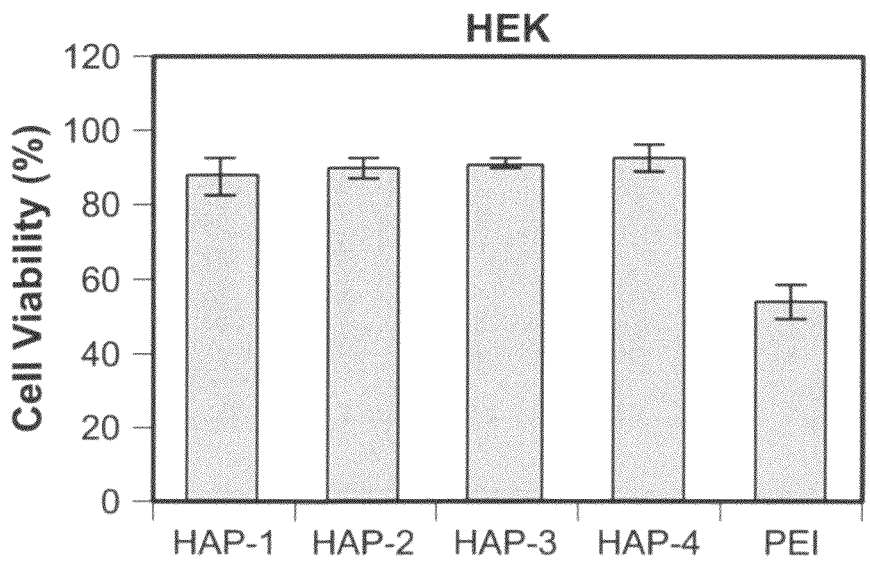
Figure 6C:
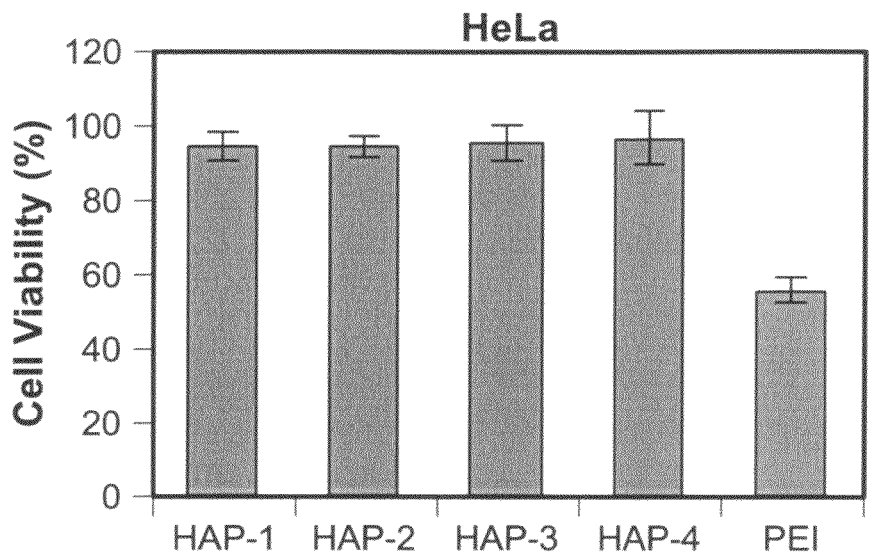
Figure 6D:
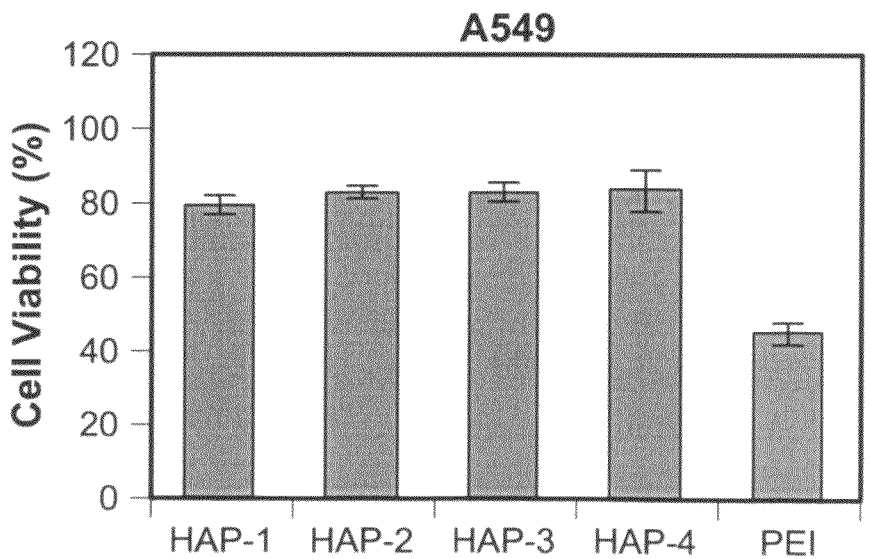

FIG. 5: Measurement of nanoparticle/DNA interactions. DNA mobility shift assay of PEI nanoparticle/DNA and PEI/DNA complexes. Plasmid DNA (0.3 or 0.15 µg) was incubated with increasing amounts of nanoparticles and PEI, respectively in a buffer containing HEPES/NaCl. The values mentioned correspond to the amount of nanoparticles (µg) used in a 20 µl reaction to condense pDNA.

FIG. 6 Cytotoxicity assay of PEI nanoparticle/DNA and native PEI/DNA complexes on various cell lines. Cells were treated with PEI nanoparticle/DNA and native PEI/DNA complexes, as described in materials and methods, and cytotoxicity was determined by MTT assay. Percent cell viability is expressed relative to the control cells. Each point represents the mean of two independent experiments performed in triplicates.

(A) Cell viability of PN nanoparticle/DNA and native PEI/DNA complexes on Hela, HEK293, COS-1, A549 cells. The data of cell viability shown is obtained at sample/DNA weight by weight ratio of 3.3.

(B) Cell viability of HAP nanoparticle/DNA and native PEI/DNA complexes on HEK293 cells.

(C) Cell viability of HAP nanoparticle/DNA and native PEI/DNA complexes on Hela cells.

(D) Cell viability of HAP nanoparticle/DNA and native PEI/DNA complexes on A549 cells.

Cell viability data is shown in fig. (A, B, C) is obtained at sample/DNA weight by weight ratio of 3.3. (Error bars represents +/− standard deviation from the mean).

Figure 7A:
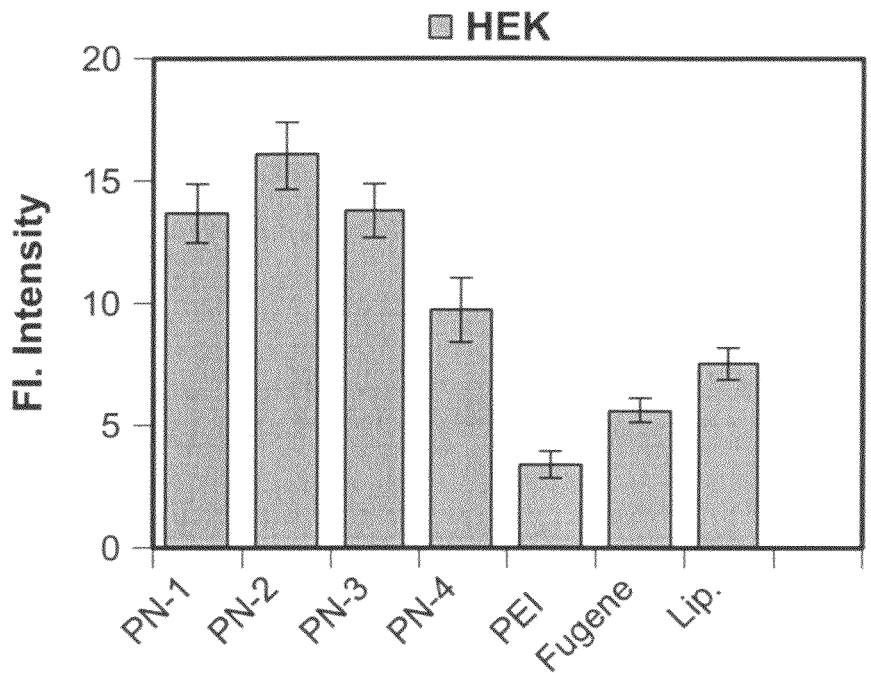
Figure 7B:
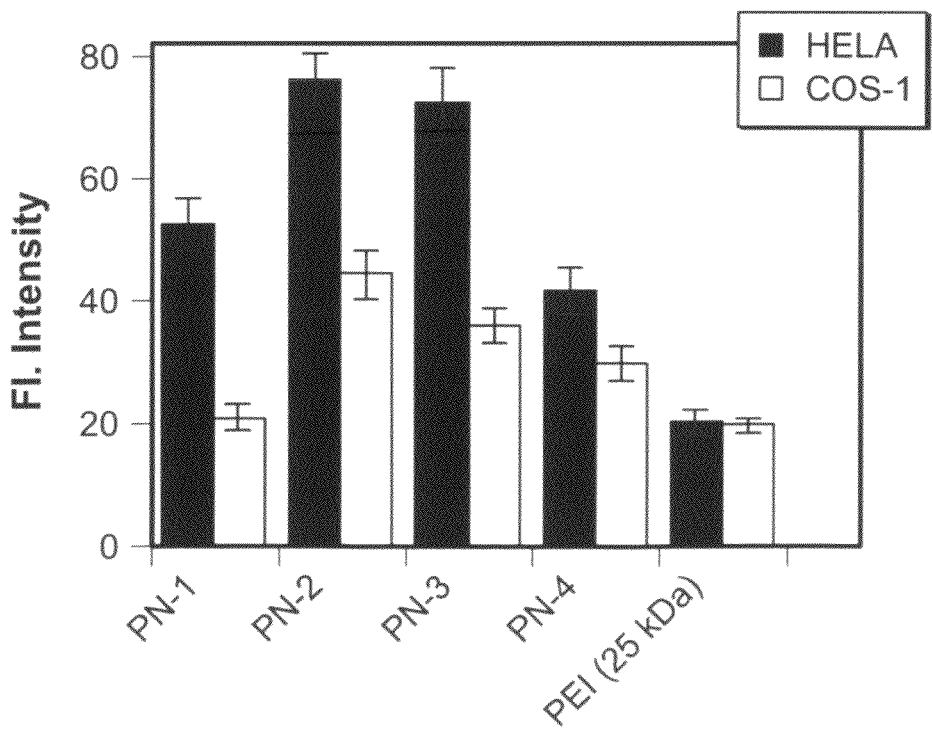
Figure 7C:
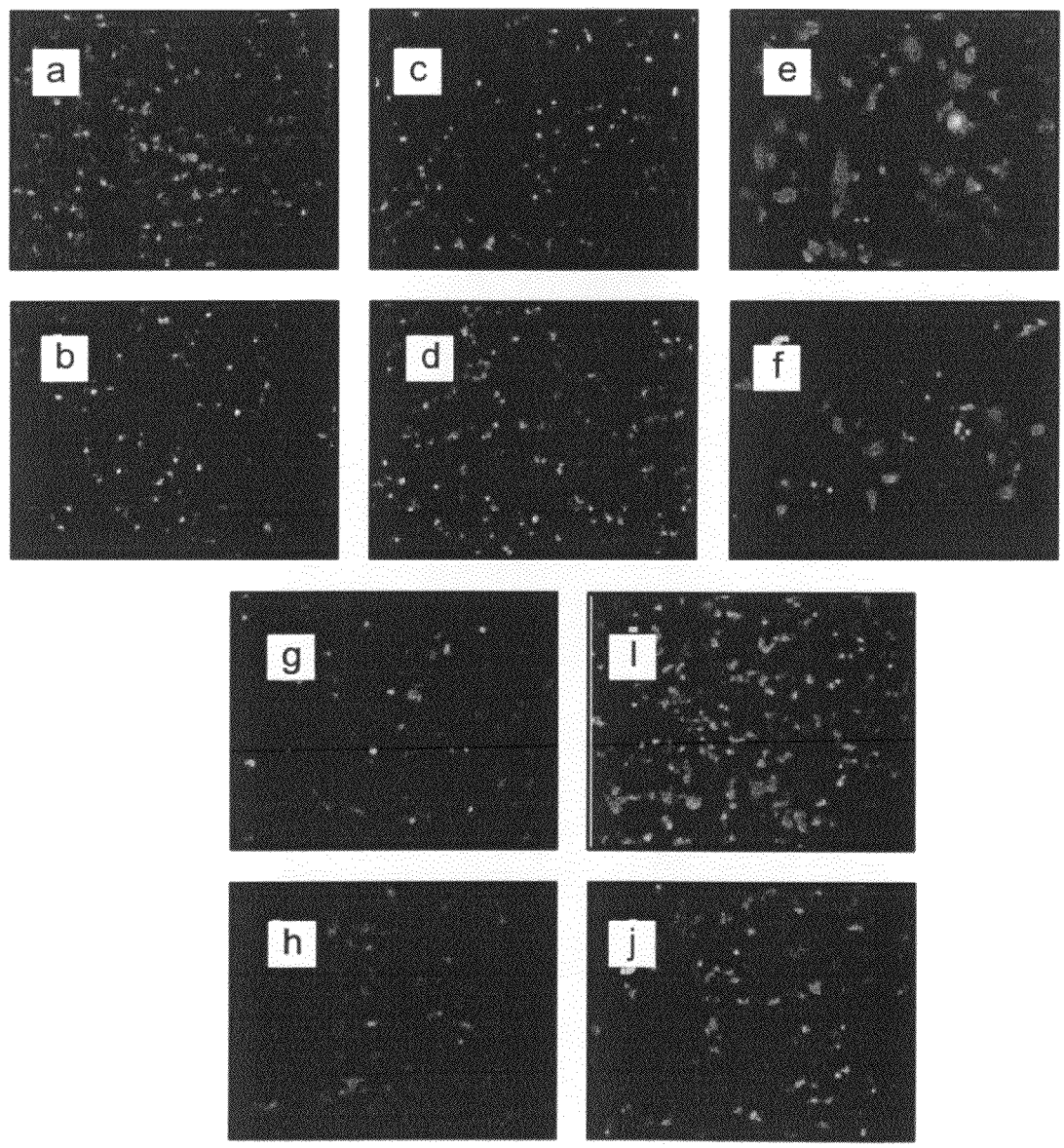
Figure 8A:
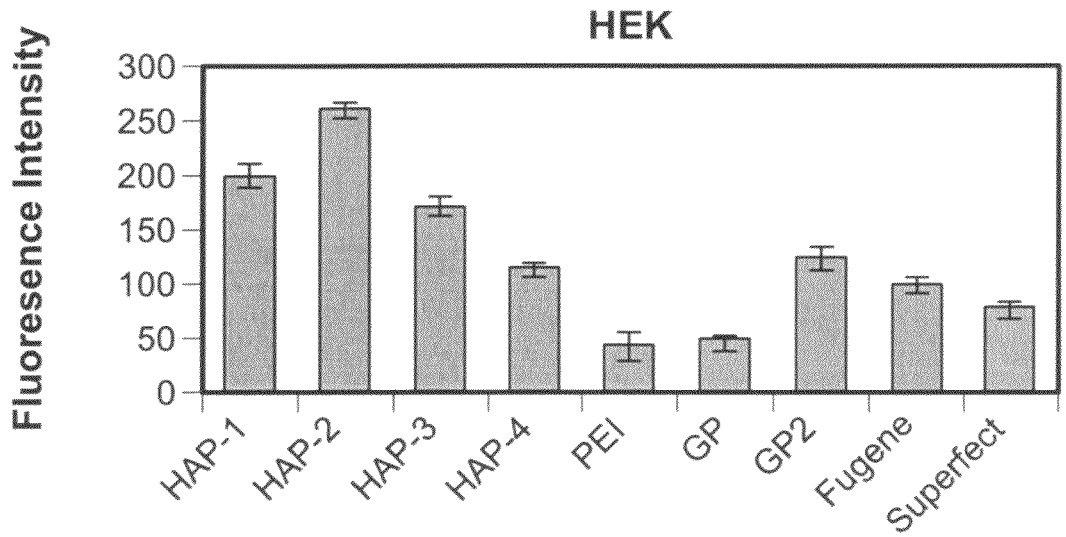
Figure 8B:
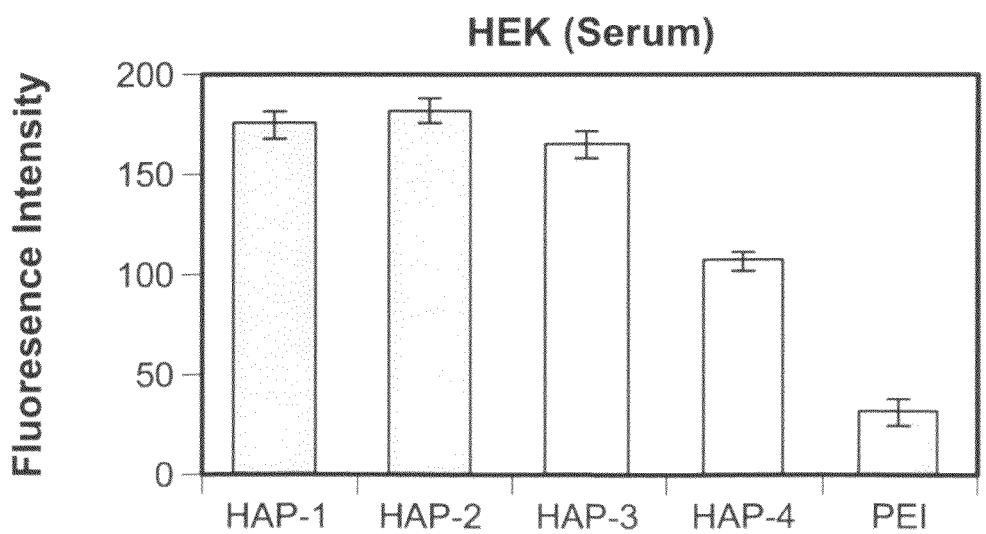
Figure 8C:
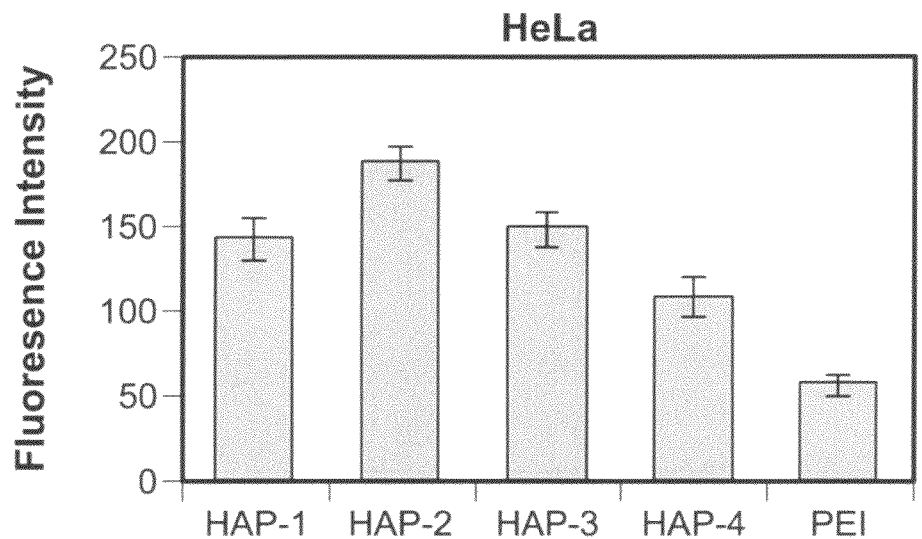
Figure 8D:
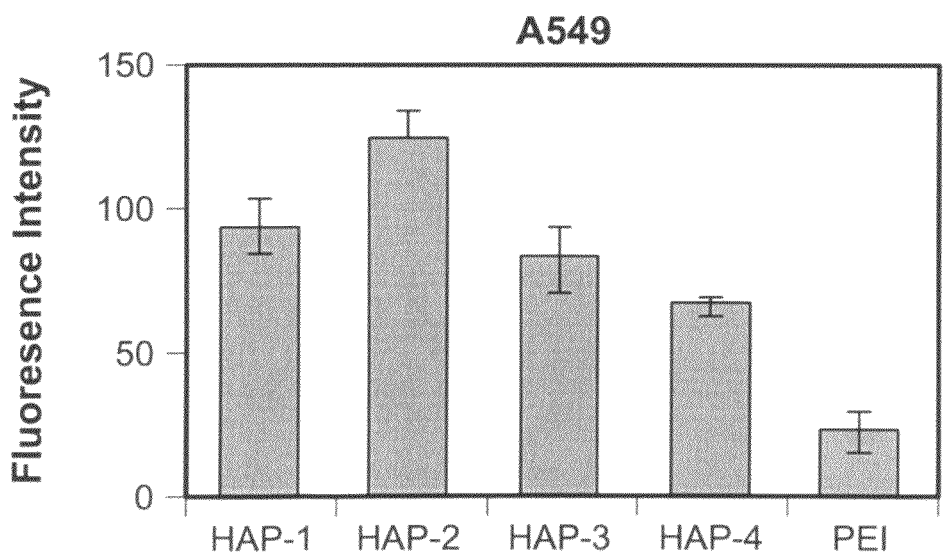

FIG. 7 GFP fluorescence intensity of cells transfected with PEI/DNA and PEI nanoparticle/DNA complexes (PN). The fluorescent intensity of GFP fluorophore in the cell lysate was measured on spectrofluorimeter and the results are expressed in terms of arbitrary units/mg total cellular protein.

The results represent the mean of two independent experiments performed in triplicates.

(A) Transfection efficiency of native PEI/DNA and PEI nanoparticle/DNA complexes, prepared at a particular weight ratios, at which highest transfection efficiency was obtained i.e. w/w=5.0 for PEI nanoparticles, w/w=0.6 for native PEI (25 kDa), Fugene and Lipofectamine 2000 on HEK293 cell line. pDNA (0.3 µg) was used for each reaction. Y-axis represents the fluorescence intensity (arbitrary units)×$10^5$ per mg of protein.

(B) Transfection efficiency on HeLa and COS-1 cells transfected with PEI/DNA and PEI nanoparticle/DNA complexes.

(C) Fluorescent intensity of HEK293, COS-1, HeLa and A549 cells transfected with PEI/DNA and PEI nanoparticle/DNA complexes and commercially available reagents, at their respective maximum transfection efficiency.

a: PN-2 (5.0:1, 75 µg/ml) HEK293; b: PEI (0.7:1, 10 µg/ml) HEK293; c: Fugene HEK293; d: Lipofectamine-2000 HEK293; e: PN-2 (5.0:1, 75 µg/ml) COS-1; f: PEI (0.7:1, 10 µg/ml) COS-1; g: PN-2 (5.0:1, 75 µg/ml) A549; h: PEI (0.7:1, 10 µg/ml) A549; i: PN-2 (5.0:1, 75 µg/ml) HELA; j: PEI (0.7:1, 10 µg/ml) HELA Images were recorded at 10× magnification. All cell lines were transfected with respective nanoparticle/DNA complexes as observed under UV, C-F1 epifluorescence filter of fluorescent microscope. The weight ratio of each sample is given in the text box below the images. (Error bars represents +/− standard deviation from the mean)

FIG. 8 GFP fluorescence intensity of cells transfected with PEI/DNA and PEI nanoparticle/DNA complexes (HAP). The fluorescent intensity of GFP fluorophore in the cell lysate was measured on spectrofluorimeter and the results are expressed in terms of arbitrary units/mg total cellular protein.

The results represent the mean of two independent experiments performed in triplicates.

(A) Transfection efficiency of native PEI/DNA and PEI nanoparticle/DNA complexes, prepared at a particular weight ratios, at which highest transfection efficiency was obtained i.e. w/w=1.0 for PEI nanoparticles, w/w=0.67 for native PEI (25 kDa), Gene Porter™, Superfect™ and Fugene™ on HEK293 cell line. pDNA (0.3 µg) was used for each reaction.

(B) Transfection efficiency on HEK293 cells transfected with PEI/DNA and PEI nanoparticle/DNA complexes (HAP) in presence of serum.

(C) Transfection efficiency on HeLa cells transfected with PEI/DNA and PEI nanoparticle/DNA complexes (HAP).

(D) Transfection efficiency on A549 cells transfected with PEI/DNA and PEI nanoparticle/DNA complexes (HAP).

Y-axis represents the fluorescence intensity (arbitrary units)×$10^5$ per mg of protein.

(Error bars represents +/− standard deviation from the mean).

Figure 9A:
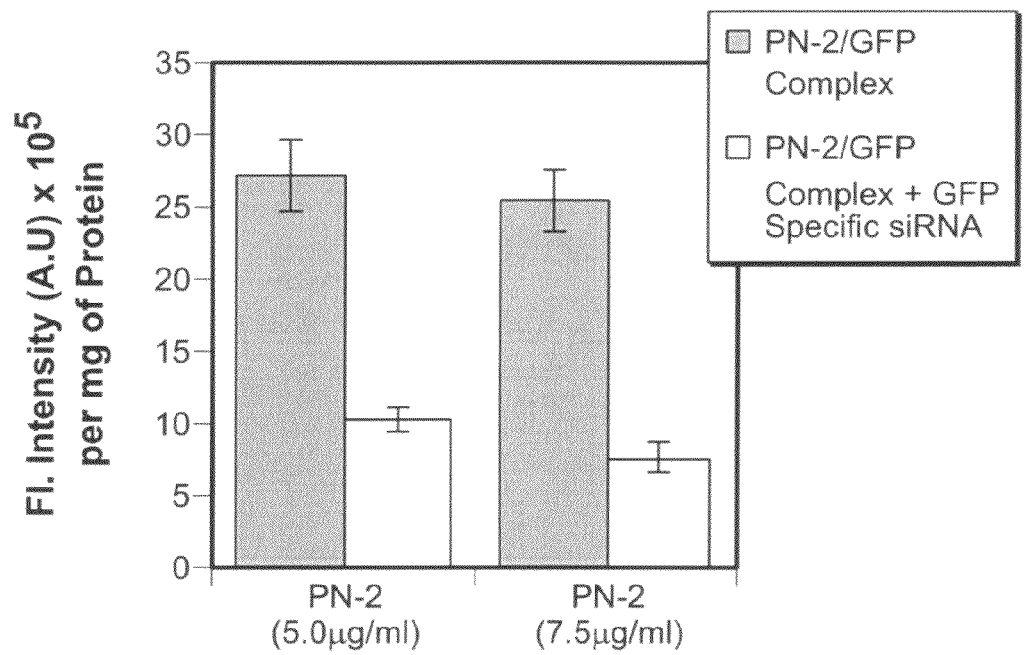
Figure 9B:
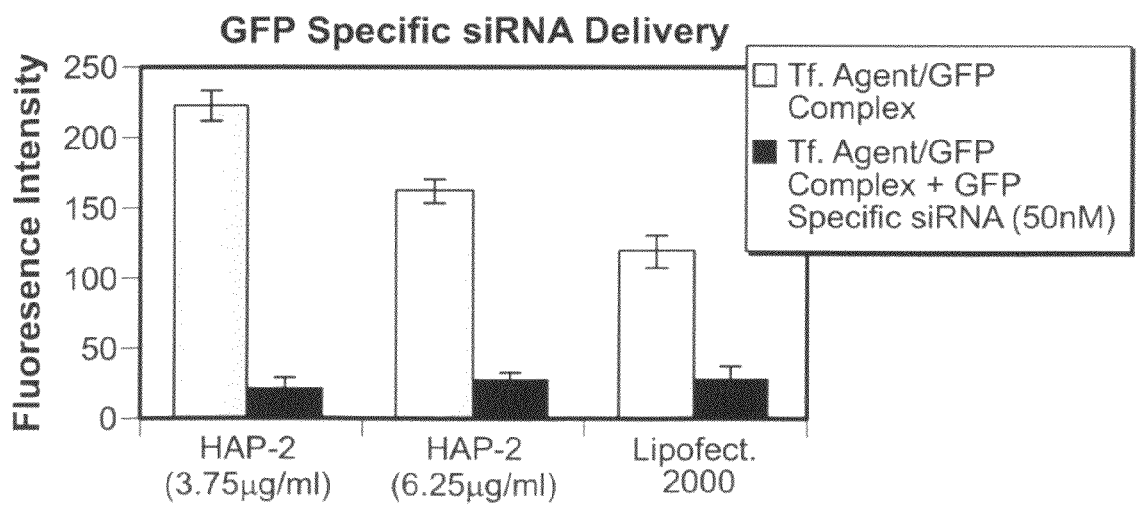

FIG. 9 PEI nanoparticles as an effective carrier of siRNA.

(A) PN-2 nanoparticles were tested for their ability to deliver GFP specific siRNA into HEK293 cells. The expression of GFP in cell lysates was reduced by ~70% as monitored by measuring fluorescence on spectrofluorimeter.

(B) HAP-2 nanoparticles were tested for their ability to deliver GFP specific siRNA into HeLa cells and compared with commercial transfection agent Lipofectamine-2000™. The expression of GFP in cell lysates was reduced by ~90% as monitored by measuring fluorescence on spectrofluorimeter.

Y-axis represents the fluorescent intensity (arbitrary units)×$10^5$ per mg of protein. Error bars represents +/− standard deviation from the mean.

DETAILS OF THE INVENTION

Present invention lies in provision of nanoparticle based efficient polymeric transfection agent with reduced toxicity by converting the amine moiety of the cationic polymer from primary to secondary, secondary to tertiary and/or further to quaternary state by crosslinking the polymer with homobifunctional crosslinker in order to obviate the shortcomings of the already existing transfecting reagents, to an extent, such as time consuming tedious chemical synthetic routes, low transfection efficiency exhibited by low molecular weight polymers, associated cytotoxicity of high molecular weight polymers, etc. One of the most attractive features of the present invention is the high transfection efficiency, and absolutely no or minimal cytotoxicity of the nanoparticles.

The steps involved in the preparation of the polymeric nanoparticles of the invention are given below:

1. Reaction of cationic polymer with crosslinker (2%-20%) to prepare the nanoparticles. The nanoparticles were prepared by crosslinking PEI with the crosslinker 1,4-butanediol diglycidyl ether (bisepoxide) (PN) or 1,6-hexanedial (HAP). In case of 1,4-butanediol diglycidyl ether (bisepoxide) crosslinked PEI nanoparticle an aqueous solution of bisepoxide (11.08 l, µl µl/ml, for 5% crosslinking) was added drop wise to a pre-heated aqueous solution of PEI (100 mg, 1 mg/ml) at 45° C. with continuous stirring over a period of 30 min and stirring was continued for 16 h at the same temperature. In case of 1,6-hexanedial (bisaldehyde)

crosslinked PEI nanoparticle To a solution of PEI (50 mg/50 ml) a solution of 1,6-hexanbisaldehyde in 50% methanol (2.7 mg for 4% cross linking, $H_2O$/MeOH=1.35 ml/1.35 ml), was added dropwise over a period of 15 min. through a 10 ml syringe with vigorous stirring. The solution was further allowed to stir at r.t. for 24 h followed by addition of sodium cynoborohydride. Thereafter the volume of the reaction mixture was reduced to half on a rotary evaporator. The remaining solution was subjected to dialysis against water for 72 h with intermittent change of water. Then after dialysis, the solution was concentrated to obtain a white residue of nanoparticles (PN-1, 88 mg, ¬ 80% yield and HAP-1, 42 mg, ~82% yield). Likewise PEI was crosslinked with bisepoxide to make 10, 15, and 20% in order to make a series of PN nanoparticle and with bisaldehyde to make 8, 12 and 16% in order to make another series of HAP nanoparticles as well. The crosslinking was controlled by adjusting the weight ratio of the crosslinker and PEI to obtain nanoparticles in ~80-90% yield.

2. Characterization of the prepared nanoparticles assessing the surface charge (zeta potential), size (dynamic light scattering) and surface morphology (atomic force microscopy and transmission electron microscopy). The particle size and zeta potential of nanoparticles and their DNA complexes were measured on Zetasizer Nano-ZS. Briefly, a known amount of lyophilized nanoparticles (200 μg) was suspended in de-ionized water (1.0 ml). Nanoparticles/DNA complexes were prepared by incubating the nanoparticles and pDNA (4 μg) in de-ionized water for 20 min at room temperature. The size of the nanoparticles and DNA complexes was also determined by atomic force microscopy using PicoSPM System operating in acoustic mode. Briefly, a solution (2-3 μl) of each nanoparticles was deposited on a freshly split untreated mica strip and allowed to dry for 5 min at room temperature. Subsequently, the mica surface was imaged. Particle size was obtained using SPIP software, an image analyzing software for scanning probe microscopy.

3. DNA retardation assay by varying the amount of nanoparticles. The electrostatic interactions between the positively charged nanoparticles and negatively charged pDNA result in the neutralization of negative charge of pDNA, which subsequently retards its mobility under the influence of electric field. To determine the optimal concentration required for complete retardation of DNA, PEI nanoparticles were incubated with pDNA at different weight ratios, keeping the amount of pDNA constant and retardation was analyzed on 0.8% agarose gel. A series of different nanoparticles to pDNA weight ratios was prepared (20 μl of sample contains 0.3 μg of pDNA). To prepare the samples, pDNA was mixed with PEI (25 kDa) (w/w ratio of 0.2, 0.3, 0.4) and PEI nanoparticles (w/w ratios of 0.6, 1.3, 2.0, 2.7 in case of PN and w/w ratio of 0.33, 0.5, 0.67 in case of HAP nanoparticle) in a 20 mM HEPES buffer, pH 7.4 containing 150 mM NaCl (in case of PN) or in 5% dextrose solution (in case of HAP nanoparticle) and incubated for 30 min at room temperature. The PEI/DNA complexes and nanoplexes, thus formed, were mixed with the loading buffer containing tracking dye (xylene cyanol) and electrophoresed at 100V for 45 min in TAE buffer (40 mM Tris-HCl, 1% (v/v) acetic acid, 1 mM EDTA). The gels were stained by ethidium bromide (0.2 mg/ml) and the bands corresponding to pDNA were visualized under a UV transilluminator 4. In order to evaluate the cytotoxicity of the prepared nanoparticles were used for in vitro transfection. HeLa cells were split one day prior to transfection and plated in 96-well plates at a density of $10^4$ cells/well in DMEM containing 10% FBS. After stipulated time, the media was aspirated from the wells and the cells were washed with serum free DMEM. DNA complexes with PEI (at w/w ratios 0.6, 1.0, 1.6, 3.3, 5.0) and PEI nanoparticles (at w/w ratios 3.3, 5.0, 6.6, 8.3 in case of PN and at w/w ratio 0.67, 1.0, 1.67, 2.33 in case of HAP nanoparticle) were prepared, as described in the DNA mobility shift assay. The toxicity of poly- and nanoplexes was ascertained by MTT colorimetric assay. After 36 h, the transfected cells were processed for MTT assay and the absorbance was recorded on an ELISA plate reader (MRX, Dynatech Laboratories) set at 540 nm. From the data, the percent cell viability was calculated. Similarly, the experiments were performed in various cell lines as HEK293, HeLa, COS-1 and A549.

5. Assessment of the transfection efficiency of the nanoparticles in various cell lines. HEK 293, A549, HeLa and COS-1 cells were seeded in a 96-well cell culture plate 16 h prior to the experiment. Complexes with DNA were prepared with PEI, PEI nanoparticles (PN, HAP). Lipofectamine 2000, Superfect™, Gene Porter 2™ and Fugene were used as positive controls following the standard protocols using the same amount of DNA as used for other samples. Similarly, the transfection was carried out with siRNA (50-100 nM) encoded for GFP in HEK293 and HeLa cells using nanoparticles (PN-2 and HAP-2). After 36 h, the cells, transfected with GFP reporter gene, were observed under Nikon Eclipse TE 2000-S inverted microscope. All the experiments were repeated thrice and the standard deviation (i) was calculated. The GFP, expressed in the cells, was quantified by measuring the fluorescence intensity. The wells of the plate containing cells were washed once with PBS, followed by lysis with 100 μl lysis buffer (10 mM Tris-HCl, pH 7.4, 0.5% SDS and 1 mM EDTA) and incubated in a shaker for 15-20 min at 25° C. Lysate (10 μl) was used to estimate the expressed reporter gene product, green fluorescent protein (GFP), spectrofluorometrically at an excitation wavelength 488 nm and emission at 509 nm. Background fluorescence and auto-fluorescence were determined using mock treated cells (cells without naked DNA). The total protein content in cell lysate from each well was estimated using Bradford's reagent (Bio-Rad), taking BSA as a standard. The level of fluorescence intensity of GFP was calculated by subtracting the background values and normalized against protein concentration in cell extracts. The data is reported as arbitrary unit (A.U.)/mg of cellular protein and represents mean±standard deviation for triplicate samples.

The following Examples describe the present invention. These Examples are provided for the purpose of illustration only and the invention should in no way be construed as being limited to these examples, but rather should be construed to encompass any and all variations which become evident as a result of the teaching provided herein.

EXAMPLE 1

The positive charge of cationic polymer polyethyleneimine (PEI) (Mw 1 kDa-800 kDa) was partially shielded on crosslinking with a homobifunctional hydrophobic reagent, with epoxide functionality, named 1,4-butanediol diglycidyl ether (bisepoxide). In order to substitute 5% amines of PEI, bisepoxide (11.08 μl, 1 μl/ml, dd water, 45° C.) was added dropwise to a pre-heated (45° C.) solution of PEI (100 mg, 1 mg/ml) with continuous stirring maintaining the temperature at 45° C. for 16 h. Then the volume of the reaction mixture was reduced to half on a rotary evaporator. The remaining solution was subjected to dialysis against water for 72 h with intermittent change of water. Thereafter, the solution was concentrated in a speed vac to obtain a white residue of nanoparticles (PN-1, 88 mg, ~80% yield) as reported by Swami et al. (Biochemical and Biophysical Research Communications 362 (2007) 835-841.).

EXAMPLE 2

In an attempt to realize 10% substitution of amines in PEI, bisepoxide (22.16 µl, 1 µl/ml, dd water, 45° C.) was added dropwise to a solution of PEI (100 mg, 1 mg/ml), with continuous stirring and subsequently the reaction was carried out as described above.

EXAMPLE 3

With the purpose of substituting 15% amines of PEI, bisepoxide (33.24 µl, 1 µl/ml, dd water, 45° C.) was added dropwise to a solution of PEI (100 mg, 1 mg/ml), with continuous stirring. The reaction was carried out as described in example 2.

EXAMPLE 4

With the intention of substituting 20% amines of PEI, bisepoxide (44.32 µl, 1 µl/ml, dd water, 45° C.) was added dropwise to a solution of PEI (100 mg, 1 mg/ml), with continuous stirring, with continuous stirring and the reaction was conducted as mentioned above.

With the purpose of substituting 15% amines of PEI, bisepoxide (22.16 µl, 1 µl/ml, dd water, 45° C.) was added dropwise to a solution of PEI (100 mg, 1 mg/ml), with continuous stirring. The reaction was carried out as described in example 2.

EXAMPLE 5

With the intention of substituting 20% amines of PEI, bisepoxide (22.16 µl, 11/ml, dd water, 45° C.) was added dropwise to a solution of PEI (100 mg, 1 mg/ml), with continuous stirring, with continuous stirring and the reaction was conducted as mentioned above.

EXAMPLE 6

The positive charge of cationic polymer polyethyleneimine (PEI) (Mw 1 kDa-800 kDa) was partially shielded on crosslinking with a homobifunctional hydrophobic reagent, with aldehyde functionality, named 1,6-hexanedial (bisaldehyde). To a solution of PEI (50 mg/50 ml) a solution of 1,6-hexanbisaldehyde in 50% methanol (2.7 mg for 4% cross linking, $H_2O$/MeOH=1.35 ml/1.35 ml), was added dropwise over a period of 15 min. through a 10 ml syringe with vigorous stirring. The solution was further allowed to stir at r.t. for 24 h followed by addition of sodium cyanoborohydride. Further the solution was dialyzed using 12 kDa cut off membrane against d.d. water for 3 days with intermittent change of water. The solution was finally lyophilized in a speed vac. To obtain cross linked nanoparticles of PEI in 82% yield.

EXAMPLE 7

The positive charge of cationic polymer polyethyleneimine (PEI) (Mw 1 kDa-800 kDa) was partially shielded on crosslinking with a homobifunctional hydrophobic reagent, with aldehyde functionality, named 1,6-hexanedial (bisaldehyde). To a solution of PEI (50 mg/50 ml) a solution of 1,6-hexanbisaldehyde in 50% methanol (5.4 mg for 8% cross linking, $H_2O$/MeOH=2.7 ml/2.7 ml), was added dropwise over a period of 15 min. through a 10 ml syringe with vigorous stirring. The solution was further allowed to stir at r.t. for 24 h followed by addition of sodium cyanoborohydride. Further the solution was dialyzed using 12 kDa cut off membrane against d.d. water for 3 days with intermittent change of water. The solution was finally lyophilized in a speed vac. To obtain cross linked nanoparticles of PEI in 80% yield.

EXAMPLE 8

The density of the residual primary amines in the nanoparticles synthesised by crosslinking PEI with bisepoxide or bisaldehyde, was determined by TNBS (2,4,6-trinitrobenzene sulfonic acid) assay of amines was determined following the standard protocol (Tseng et al., 2004) (Table 3). These nanoparticles were further characterized by FTIR and $^1$H NMR (Table 4). The qualitative functional group analysis in PEI-nanoparticles by FTIR (KBr) yielded the peaks at 3435 (—NH stretching), 2856, 1638 (—CO stretching), 1454 (—NH bending).

EXAMPLE 9

Size and Zeta Potential Measurements

The particle size and zeta potential of nanoparticles and their DNA complexes were measured on Zetasizer Nano—ZS as described in the published report (7). The results of the nanoparticle of PN and HAP series are summarized in Table-1 & 2 respectively and As shown in FIG. 1, AFM (atomic force microscopic) images of PEI nanoparticles, (A) native PN-2 (32-40 nm) and (B) DNA loaded PN-2 nanoplexes (55-60 nm) (C) HAP-2 (40-55 nm) and (D) DNA loaded HAP-2 nanoplex (60-75 nm) revealed monodisperse spherical complexes in the nanometer range. DLS experiment also showed similar trend but the size of the nanoparticles and DNA complexes were larger compared to that of AFM. The larger size of particles in DLS is due to the measurement of hydrodynamic diameter. FIG. 3 Size distribution obtained by TEM images of PEI nanoparticles, (i) PN-2 nanoparticles with average size of ~35 nm, (ii) PN-3 nanoparticles with the average size of ~27 nm.

EXAMPLE 10

DNA Retardation Assays

A known amount of plasmid DNA, (0.3 µg) was mixed with nanoparticles at different weight ratios in 20 mM HEPES buffer, pH 7.4 containing 150 mM NaCl or in 5% dextrose and incubated for 30 min at room temperature. The nanoparticles/DNA complexes, thus formed, were mixed with loading buffer containing a tracking dye (xylene cyanol) and loaded into individual wells of 0.8% agarose gel and electrophoresed at 100 V for 45 min. The gels were stained by ethidium bromide and the bands corresponding to plasmid DNA were visualized under UV light. Increasing the amount of PEI nanoparticles in DNA complexes lead to decreased electrophoretic mobility. The native PEI polymer completely inhibited the migration of pDNA at w/w ratio of 0.2 (FIG. 5).

EXAMPLE 11

In Vitro Transfection Studies

HEK293 cells were seeded onto 96-well plates at a density of $10^4$ cells per well. After incubation for 16 h, the media was aspirated from the wells and the cells washed once with serum free DMEM. Nanoparticles/DNA complexes were prepared as described in the retardation assay. Subsequently, the complexes were diluted with serum-free DMEM to a final volume of 80 µl (transfection medium) and added gently to each well followed by incubation at 37° C. in humidified 5% $CO_2$ atmosphere. After 4 h, the transfection mixture was replaced by 200 µl fresh growth medium (DMEM with 10% FCS) and the cells were further incubated for 36 h. siRNA (100 nM) was also added at the time of preparation of nanoparticles/DNA complexes and transfected into HEK293 cell line in a similar manner. Thereafter, the cells, transfected with GFP reporter gene, were observed under an inverted fluorescent microscope at 10× magnification. Similar experiments were also carried out on HeLa, COS-1 and A549 cell lines. All the experiments were repeated at least thrice. (FIGS. 7 & 8)

EXAMPLE 12

HEK293 and HeLa cells were seeded onto 96-well plates at a density of $10^4$ cells per well. After incubation for 16 h, the media was aspirated from the wells and the cells washed once with serum free DMEM. Nanoparticles/DNA complexes were prepared as described in the retardation assay. Subsequently, siRNA (100 nM) was also added at the time of preparation of nanoparticles/DNA complexes and transfected into the cells in a similar manner. Thereafter, the cells, transfected with GFP reporter gene, were observed under an inverted fluorescent microscope at 10× magnification. GFP specific siRNA was able to inhibit the GFP expression by ~62-70% in case of PN-2 nanoparticle and ~90% in case of HAP-2 nanoparticle as compared with the mock control (cells transfected with PEI nanoparticles/DNA complexes) and this inhibition was significant and repeatable as three independent experiments were performed in triplicates (FIG. 9).

EXAMPLE 13

Analysis of EGFP Expression

The GFP expressed in the cells was quantified by measuring the fluorescence intensity. After 36 h, the transfected cells were washed once with PBS followed by lysis in a buffer containing 10 mM Tris HCl, pH 7.4, 0.5% SDS and 1 mM EDTA, and incubated in a shaker for 15-20 min at 25° C. Lysate (20 µl) was used to estimate the expressed reporter gene product, green fluorescent protein (GFP), spectrofluorometrically. Background and autofluorescence were determined using mock treated cells. The total protein content in cell lysate from each well was estimated using Bradford's reagent (Biorad) by taking BSA as a standard. The fluorescence intensity of GFP in transfected cells was calculated by subtracting the background values and normalized against protein concentration in cell extracts. The data was reported as arbitrary units (A.U.)/mg of cellular protein and represents mean±standard deviation for triplicate samples.

The transfection efficiency of polymeric transfection agent (PEI crosslinked with 1,4-butanediol diglycidyl ether, PN series) is 4.7 fold with respect to native PEI in case of HEK293 cells, 2.2 fold w.r.t. PEI in case of COS-1 cells and 3.8 fold w.r.t. PEI in case of HeLa cells. The transfection efficiency of polymeric transfection agent (PEI crosslinked with 1,6-hexanedial, HAP series) is 6.1 fold with respect to PEI in case of HEK293 cells, 3.5 fold w.r.t. PEI in case of HeLa cells; 1.9 fold w.r.t. PEI in case of A549 cells. Also the transfection efficiency of polymeric transfection agent (PEI crosslinked with 1,4-butanediol diglycidyl ether) as compared to commercial transfection agents is 2.9 fold w.r.t. Fugene™ and 2.1 fold w.r.t. Lipofectamine-2000™ in case of HEK293 cells. the transfection efficiency of polymeric transfection agent (PEI crosslinked with 1,6-hexanedial) as compared to commercial transfection agents is 2.1 fold w.r.t. gene porter 2™, 2.2 fold w.r.t. Fugene™ and 3.6 fold w.r.t. Superfect™ in case of HEK293 cells as shown in FIGS. 7 & 8.

EXAMPLE 14

Cytotoxicity Assay

The cytotoxicity associated with polycations has always been a concern in their use as DNA carriers. To assess the cytotoxicity of nanoparticle/DNA complexes, the cells were transfected as described above. After 36 h, MTT (3-(4,5-dimethylthiazol-2-yl)-2,5-diphenyltetrazolium bromide) (0.5 mg dissolved in 1.0 ml of DMEM) was added to the HeLa cells and incubated for 2 h. Then the supernatant was aspirated, and the formazan crystals were suspended in 100 µl isopropanol containing 0.06 M HCl and 0.5% SDS. Aliquots were drawn from each well and the intensity of color was measured spectrophotometrically in an ELISA plate reader (MRX, Dynatech Laboratories) at 540 nm. Untreated cells were taken as control with 100% viability and cells without addition of MTT were used as blank to calibrate the spectrophotometer to zero absorbance. The relative cell viability (%) compared to control cells was calculated by $[abs]_{sample}/[abs]_{control} \times 100$. It was observed that the cells treated with alginate containing complexes yielded an almost similar viability like controls (untreated cells) in HeLa cells line. Further, an increase in percent crosslinking improved the cell viability and also supported cell growth in some cases. Similar experiments were performed in HEK293, COS-1 and A549 cell lines (FIG. 6).

ADVANTAGES OF THE INVENTION

1. The process of synthesizing the polymeric transfection vector is simple and devoid of tedious chemical synthetic routes.
2. The reagents employed in the invention are easily available and need no coupling reagent.
3. The reactions involved in the preparation of nanoparticles are clean and do not result in any harmful side product.
4. The transfection reagent efficiently transfects a variety of cell lines. The transfection efficiency is enhanced manifolds in different cell lines compared to the standards (bPEI 25 kDa, gene porter 2, superfect, Lipofectamine-2000, fugene, etc.).
5. There is no observed cytotoxicity associated with the nanoparticles.

TABLE 1

| Sample | Average particle size in nm (±S.D.) | | | Zeta potential in mV (±S.D.) | | |
|---|---|---|---|---|---|---|
| | PN (in dH$_2$O) | DNA loaded PN (in dH$_2$O) | DNA loaded PN (in serum) | PN (in dH$_2$O) | DNA loaded PN (in dH$_2$O) | DNA loaded PN (in serum) |
| PN-1 | 76.9 (4.6) | 116.8 (3.5) | 89.8 (6.2) | 41.1 (3.1) | 30.2 (1.2) | −7.9 (0.8) |
| PN-2 | 73.7 (3.7) | 110.4 (3.4) | 86.2 (5.1) | 39.8 (2.9) | 29.1 (1.8) | −7.7 (1.2) |
| PN-3 | 70.9 (4.4) | 105.5 (6.8) | 83.5 (4.8) | 37.6 (3.1) | 27.2 (1.6) | −7.4 (1.4) |
| PN-4 | 68.5 (5.6) | 102.3 (3.2) | 82.4 (6.5) | 36.0 (2.1) | 26.8 (1.2) | −7.5 (0.9) |
| PEI | — | 588.9 (10.9) | 397.8 (15.2) | 44.5 (5.9) | 35.7 (4.5) | −14.7 (3.2) |

TABLE 2

| Sample | Average particle size in nm (±S.D.) | | | Zeta potential in mV (±S.D.) | | |
|---|---|---|---|---|---|---|
| | HAP (in dH$_2$O) | DNA loaded HAP (in dH$_2$O) | DNA loaded HAP (in serum) | HAP (in dH$_2$O) | DNA loaded HAP (in dH$_2$O) | DNA loaded HAP (in serum) |
| HAP-1 | 173 (10.2) | 202 (6.3) | 112 (6.8) | 33.6 (1.2) | 25.7 (1.3) | −9.7 (0.9) |
| HAP-2 | 118 (8.4) | 149 (5.1) | 95 (7.4) | 31.1 (1.4) | 24.3 (1.8) | −9.8 (1.2) |
| HAP-3 | 90 (8.1) | 122 (5.2) | 87 (8.3) | 28.5 (1.2) | 20.1 (1.6) | −9.5 (1.2) |
| HAP-4 | 78 (6.6) | 104 (4.8) | 59 (7.0) | 25.8 (1.7) | 18.8 (1.4) | −9.4 (1.3) |
| PEI | — | 396 (14.8) | 341 (12.3) | 40.7 (6.2) | 33.5 (4.5) | −12.5 (2.4) |

TABLE 3

| S. No. | Sample | Attempted substitution (%) | Obtained substitution (%) by NMR |
|---|---|---|---|
| 1 | PN-1 | 5 | 3.27 |
| 2 | PN-2 | 10 | 7.5 |
| 3 | PN-3 | 15 | 12.9 |
| 4 | PN-4 | 20 | 19.8 |

TABLE 4

| S. No. | Samples | Attemped (%) substitution | Realised (%) substitution (TNBS) |
|---|---|---|---|
| 1 | HAP-1 | 8 | 7.825 |
| 2 | HAP-2 | 16 | 15.669 |
| 3 | HAP-3 | 24 | 22.071 |
| 4 | HAP-4 | 32 | 31.104 |

TABLE 5

| S. No. | Samples | IC$_{50}$ |
|---|---|---|
| 1 | HAP-1 | 60 |
| 2 | HAP-2 | 60 |
| 3 | HAP-3 | 60 |
| 4 | HAP-4 | 60 |
| 5 | PEI | 7.5 |

We claim:

1. A crosslinked polyethylenimine (PEI) nanoparticle based nucleic acid transfection agent wherein polyethylenimine is crosslinked with a cross linker comprising a C2 to C8 carbon chain, the crosslinker content ranges between 3.27-19.8% by weight of the total weight of the nanoparticle, wherein the nanoparticle size is between 20-600 nm and zeta potential of the crosslinked polyethyleneimine nanoparticle ranges from +5 to 50 mV.

2. The polymeric nanoparticle based transfection agent according to claim 1, wherein the polymeric transfection agent is polyethylenimine crosslinked with 1,4-butanediol diglycidyl ether, to convert toxic primary state of amine of the cationic polymer to less toxic secondary, tertiary and quaternary state.

3. The polymeric nanoparticle based transfection agent according to claim 2, wherein the transfection efficiency of the polymeric transfection agent (PEI crosslinked with 1,4-butanediol diglycidyl ether) is 3 to 4.7 fold with respect to PEI in case of HEK293 cells, 1.0 to 2.2 fold with respect to PEI in case of COS-1 cells and 2.0 to 3.8 fold with respect to PEI in case of HeLa cells.

4. The polymeric nanoparticle based transfection agent according to claim 2, wherein the transfection efficiency of the polymeric transfection agent (PEI crosslinked with 1,4-butanediol diglycidyl ether) as compared to the commercial transfection agents is 1.7 to 2.9 fold higher than Fugene™ and 1.3 to 2.1 fold higher than Lipofectamine-2000™ in case of HEK293 cells.

5. The polymeric nanoparticle based transfection agent according to claim 2, wherein the cell viability of the polymeric transfection agent (PEI crosslinked with 1,4-butanediol diglycidyl ether) is in the range of 90 to 93% in case of HeLa cells; 80 to 85% in case of HEK293 cells; 90 to 95% in case of COS-1 cells and 68-82% in case of A549 cells.

6. The polymeric nanoparticle based transfection agent according to claim 1, wherein the polymeric transfection agent is polyethylenimine crosslinked with 1,6-hexanedial to convert the toxic primary state of amine of the cationic polymer to less toxic secondary amines.

7. The polymeric nanoparticle based transfection agent according to claim 6, wherein the transfection efficiency of the polymeric transfection agent (PEI crosslinked with 1,6-hexanedial) is 2.4 to 6.1 fold with respect to PEI in case of HEK293 cells, 2.1 to 3.5 fold with respect to PEI in case of HeLa cells; 3.3-6.1 with respect to PEI in case of A549 cells.

8. The polymeric nanoparticle based transfection agent according to claim 6, wherein the transfection efficiency of the polymeric transfection agent (PEI crosslinked with 1,6-hexanedial) as compared to the commercial transfection agents is 0.9 to 2.1 fold with respect to gene porter 2™, 1.1 to 2.5 fold with respect to Fugene™ and 1.45 to 3.3 fold with respect to Superfect™ in HEK293 cells.

9. The polymeric nanoparticle based transfection agent according to claim 6, wherein the cell viability of the polymeric transfection agent (PEI crosslinked with 1,6-hexanedial) is in the range of 88 to 93% in case of HEK293 cells; 92 to 96% in case of HeLa cells and 80 to 82% in case of A549 cells.

10. The polymeric nanoparticle based transfection agent according to claim 1, wherein the transfection efficiency of polymeric transfection agents (PEI crosslinked with 1,4-butanedoil diglycidyl ether and 1,6-hexanedial) is several folds higher as compared to the commercial available transfection agents such as Lipofectamine2000™, genePORTER 2™, and Fugene™.

11. The polymeric nanoparticle based transfection agent according to claim 10, wherein the transfection efficiency of the polymeric transfection agent (PEI crosslinked with 1,4-butanediol diglycidyl ether) is 1.7 to 2.9 fold with respect to the commercial transfection agent Fugene™ and 1.3 to 2.1 fold with respect to the commercial transfection agent Lipofectamine-200™ in the case of $HEK_{293}$ cells.

12. The polymeric nanoparticle based transfection agent according to claim 10, wherein the transfection efficiency of the polymeric transfection agent (PEI crosslinked with 1,6-hexanedial) is 0.9 to 2.1 fold with respect to the commercial transfection agent gene porter 2™, 1.1 to 2.5 fold with respect to the commercial transfection agent Fugene™ and 1.45 to 3.3 fold with respect to the commercial transfection agent Superfect™ in the case of $HEK_{293}$ cells.

* * * * *